Figure 1:
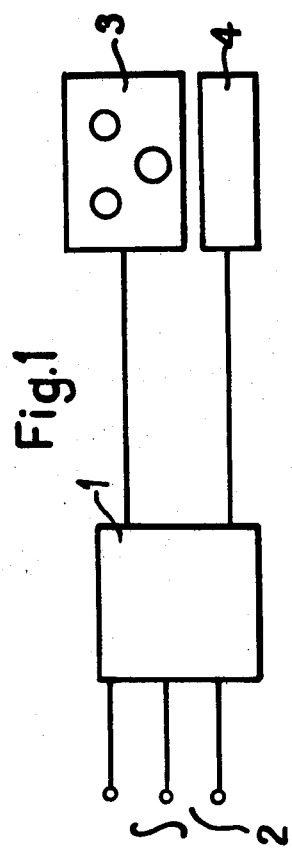

United States Patent [19]

Fellus

[11] 4,454,883
[45] Jun. 19, 1984

[54] ELECTROTHERAPEUTIC APPARATUS

[75] Inventor: Victor M. Fellus, Meudon, France

[73] Assignee: Therafield Holdings Limited, Isle of Man

[21] Appl. No.: 348,888

[22] Filed: Feb. 16, 1982

[51] Int. Cl.³ .............................................. A61N 1/40
[52] U.S. Cl. ........................................ 128/422; 128/1.5
[58] Field of Search ..................... 128/1.3, 1.5, 419 R, 128/420–423, 783, 798, 804

[56] References Cited

U.S. PATENT DOCUMENTS

| 2,882,904 | 4/1959 | Rasmussen | 128/798 |
| 3,127,895 | 4/1964 | Kendall et al. | 128/422 |
| 3,675,655 | 7/1972 | Sittner | 128/422 |
| 3,924,196 | 12/1975 | Takahashi et al. | 128/804 |
| 3,952,751 | 4/1976 | Yarger | 128/422 |
| 4,154,246 | 5/1979 | LeVeen | 128/804 |
| 4,197,851 | 4/1980 | Fellus | 128/422 |
| 4,266,532 | 5/1981 | Ryaby et al. | 128/1.5 |
| 4,384,582 | 5/1983 | Watt | 128/798 |

FOREIGN PATENT DOCUMENTS

| 2534148 | 2/1977 | Fed. Rep. of Germany | 128/422 |
| 1215110 | 4/1960 | France | 128/1.3 |
| 1255797 | 6/1961 | France . | |
| 2207733 | 6/1974 | France . | |
| 2391738 | 12/1978 | France . | |
| 2445151 | 7/1980 | France . | |
| 275614 | 8/1951 | Switzerland . | |
| 313359 | 6/1929 | United Kingdom | 128/798 |
| 2027594 | 2/1980 | United Kingdom | 128/798 |

Primary Examiner—William E. Kamm
Assistant Examiner—Mitchell J. Shein
Attorney, Agent, or Firm—Biebel, French & Nauman

[57] ABSTRACT

The present invention concerns electrotherapeutic apparatus for generating and applying to a patient's body a pulsed high frequency predominently electrical field and for generating and applying to the patient a pulsed magnetic field independent from the electrical field, the pulses of the magnetic field being applied in a predetermined relationship with the pulses of the electrical field. The apparatus includes an applicator electrode applicable directly to a patient's body and which includes at least one magnetic coil for producing a magnetic field and at least one active electrode for applying the electrical field.

21 Claims, 8 Drawing Figures

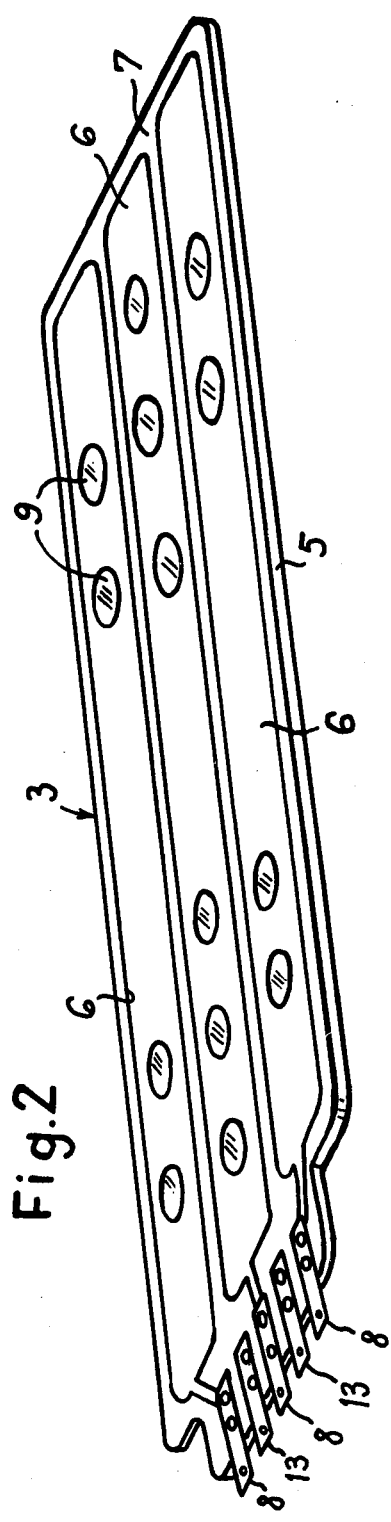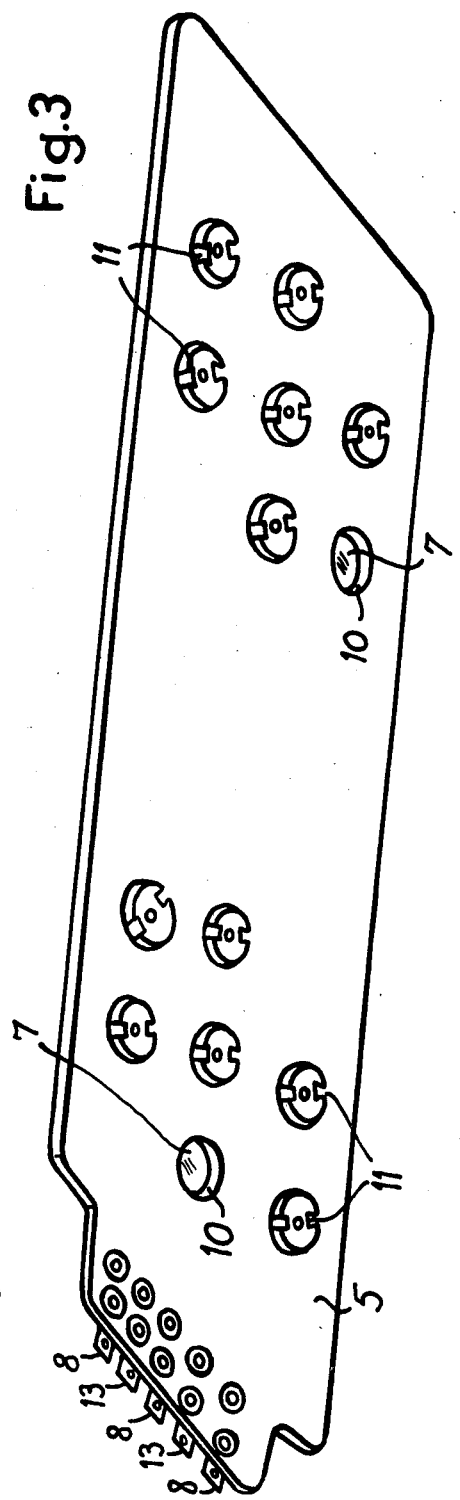

ELECTROTHERAPEUTIC APPARATUS

The present invention relates to electrotherapeutic apparatus.

Such apparatus can be applied in very many fields and in particular in all those where research, development and industry require the application of an electromagnetic field under extremely accurate conditions. Accordingly there are many kinds of apparatus in the prior art for generating electrical currents or for producing magnetic electrical or electromagnetic fields. Such apparatus may operate either as current generators or as field emitters and may do so for either temporary or long-term use on the premises of the person giving treatment or by the patient's bed. For a better understanding of the apparatus with which the present invention is concerned the basic vocabulary will be reviewed taking the example of medical and other biological applications as a basis.

When use is made of electrical currents, at least two electrodes are employed, these electrodes being applied to the patient, who becomes a conductive element in the circuit. This chiefly products various physical and chemical effects (a thermal Joule effect, ionophoresis which provides for the passage of ions through the tissues, etc) and nerve effects (a motor exciting effect). Amongst the electrical currents used are galvanic (continuous) and faradic and interrupted galvanic (pulsed).

Use has also been made in the prior art, of what have for long been known as "short waves" which are generated by so-called short-wave diathermy apparatus. One way of applying short-waves to a patient is to create a capacitive, and thus purely electrical, field by means of electrodes which may be in the form of plates or flexible pads which are positioned on either side of, and at a distance from, the patient, the patient becoming a dielectric element. The dielectric losses then give rise to heating of the body tissues. Another way of applying "short-waves" is to produce an electric field using only one electrode or plate with the patient forming an earth, spaced from the body which, again, gives rise to heating of the body tissues and could result in a sparking phenomenon between patient and electrode if the apparatus is not used correctly. Further, "short-waves" have been applied by induction coils, which may be formed by coiling a co-axial cable, and which produce a magnetic field that generates eddy currents within the body which are transformed into heat. As with plate and pad electrodes, the induction coils must be spaced from the patient if harmful effects, such as burns are to be avoided. All such "short-wave" treatments are based on the premise that the therapeutic effect is dependent upon the heating action which is ensured by high operating voltages and a continuous emission.

Apparatus is also known for producing pulses electromagnetic waves which do not produce any significant thermal effects on the patient's body. With such apparatus, the therapeutic effect is considered to be due to the applied electrical forces that are many times higher than those possible with short-wave diathermy apparatus since heat tolerance is no longer a factor. The pulsed electromagnetic waves are applied to a patient's body, by means of a coil-type electrode which must be positioned at a distance from the body, in bursts of high intensity requiring the use of even higher voltages than the short-wave diathermy apparatus to achieve the higher electrical forces considered to be necessary to obtaining the desired therapeutic effect. One form of such apparatus utilises voltages in the range of 600 to 2000 watts, has a peak power of 1400 watts and the pulsed waves produce an average induced power of about 40 watts. The electrode transfers this energy to the patient in the form of an electromagnetic field which is of high energy at the electrode.

It is also known to provide apparatus for emitting high-frequency electromagnetic waves, said apparatus comprising low-voltage power supply means, circuit means for producing high-frequency, electrical signals, said circuit means having an input and an output, means for connecting said input to said power supply means, and at least one antenna which is applicable directly to a patient's body and which is connected or connectable to the output of said circuit means, for producing at the antenna a low energy high frequency electromagnetic field without significant thermal effects on the body, said antenna comprising at least one conductor which is carried by a support of an electrically insulating material which includes a length of conductive material arranged in a predetermined pattern. Such low-voltage apparatus can utilise voltages of less than 50 volts and energies of less than 100 mW cm$^2$ of receiving surface, thereby enabling harmful thermal effects to be avoided, bulk to be considerably reduced and high-frequency emitting antenna to be used which can be placed in contact with the patient's body and which do not give to dangers, such as sparking, as can occur with high energy apparatus. It will be appreciated that the antenna of such apparatus does not set up a flow of electrical current between the apparatus and the patient, as is the case with low-frequency current emitting electrodes which operate in direct electrical contact, but produces an electromagnetic field in the body and does not need a cooperating antenna to produce the electromagnetic field.

The present invention has for an object to provide electrotherapeutic apparatus capable of treating a patient in two separate modes.

Accordingly the present invention consists in electrotherapeutic apparatus comprising means for applying to a patient's body a pulsed high-frequency electrical field and means for generating and applying to the patient a pulsed magnetic field independent from the electrical field, the arrangement being such that the pulses of the magnetic field can be applied in a predetermined relationship with pulses of the electrical field.

Preferably the means for applying the high-frequency electrical field and the magnetic field comprise a pair of applicator electrodes applicable directly to a patient's body, one applicator electrode being a neutral electrode, and the other applicator electrode comprising at least one magnetic coil for generating a magnetic field and an active electrode for cooperating with the neutral electrode to generate an electrical field.

Figure 4:
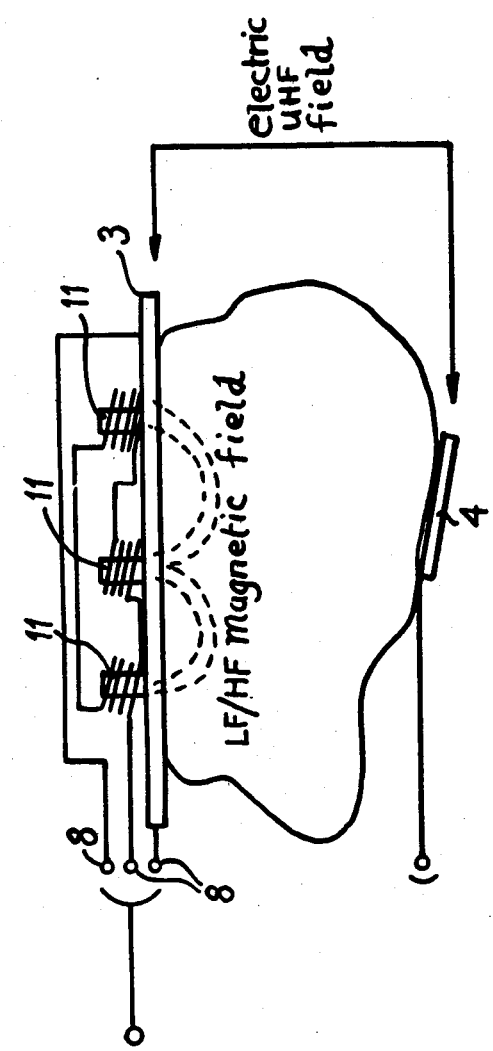
Figure 5:
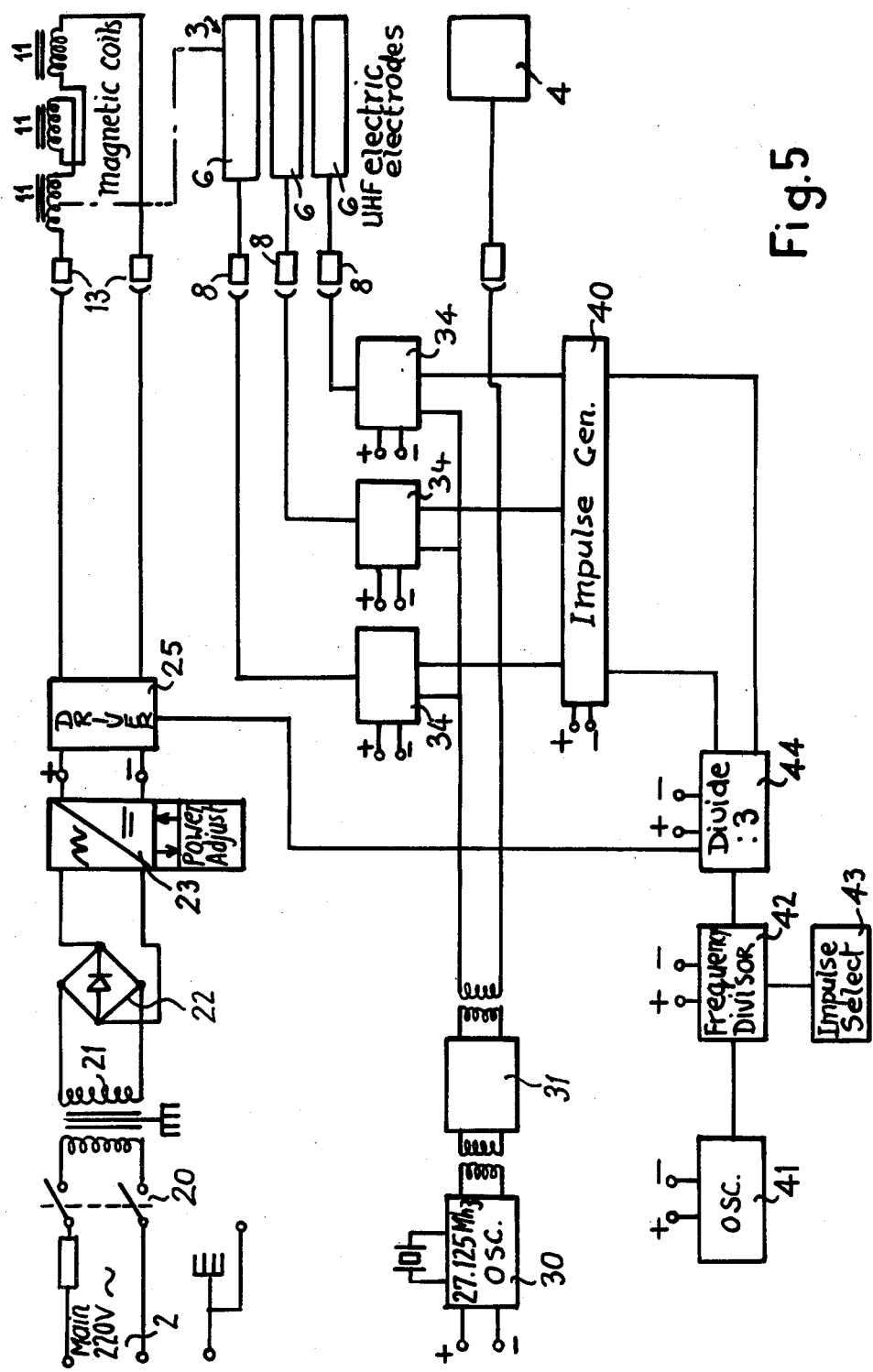
Figure 6:
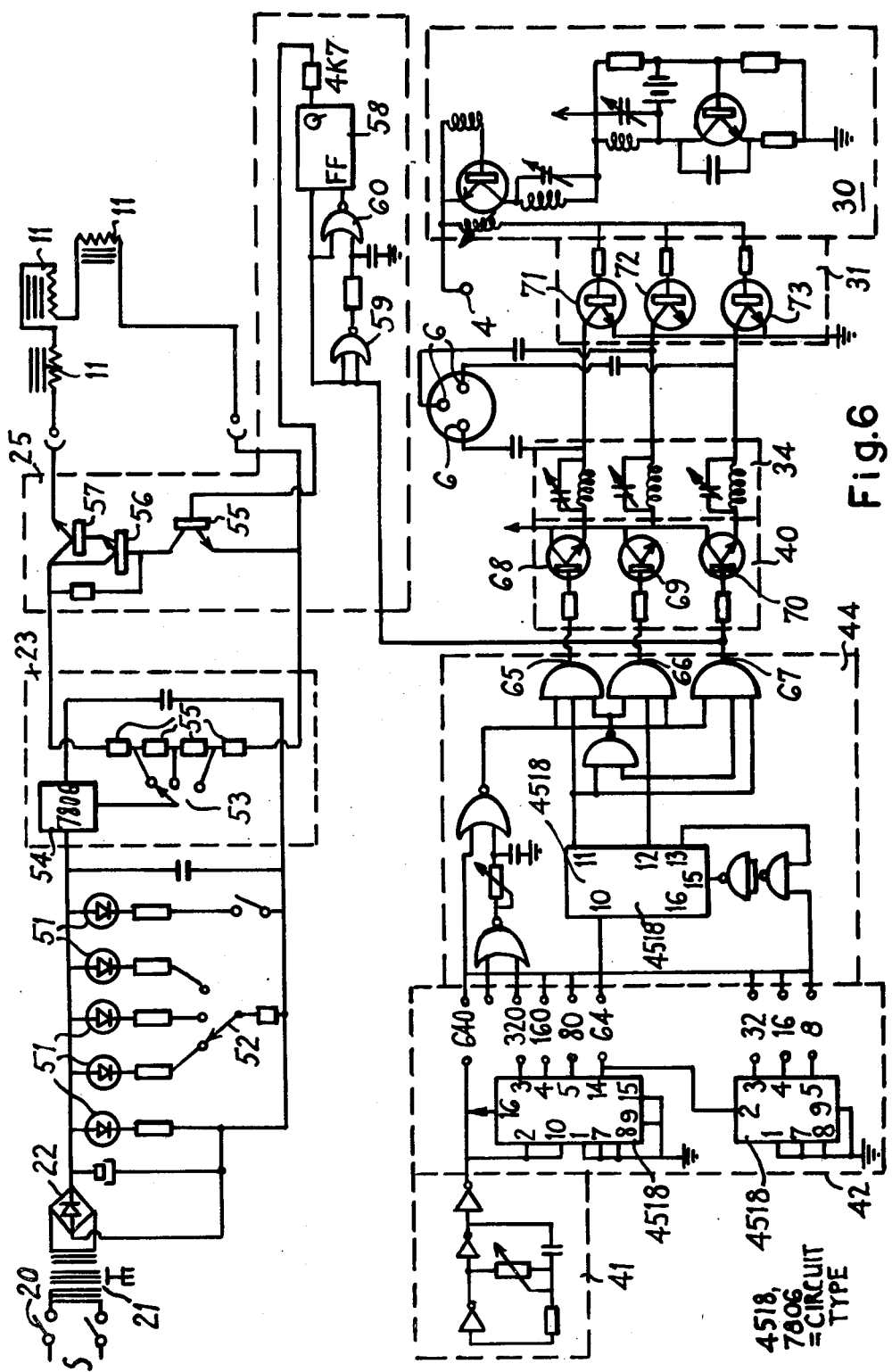
Figure 7:
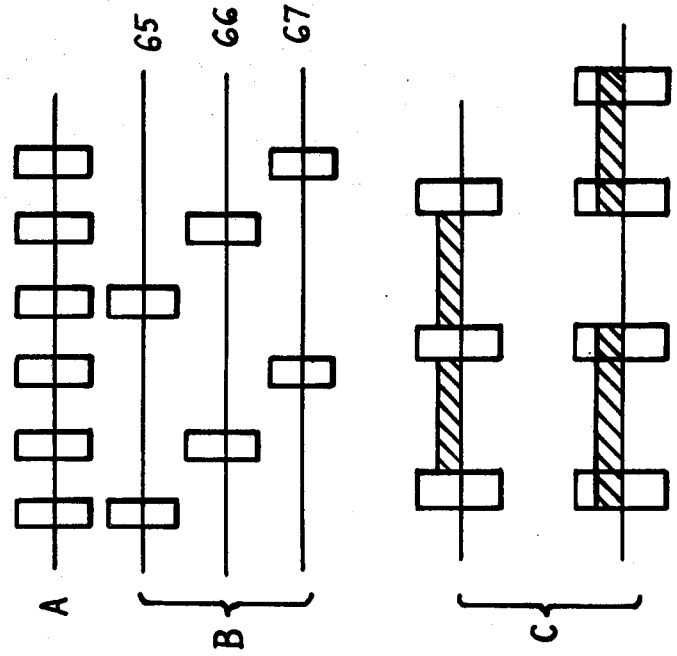

In order that the present invention may be more readily understood, reference will now be made by way of example to the accompanying drawings, in which:

FIG. 1 is a schematic block diagram of electrotherapeutic apparatus constructed in accordance with the present invention, FIGS. 2 and 3 are respectively upper and lower perspective views of an electrode for use with the apparatus of FIG. 1, FIG. 4 is a schematic section showing two electrodes in position on a patient's body, FIG. 5 is a block diagram of the apparatus shown in FIG. 1, FIG. 6 is a circuit diagram showing the components of the block diagram of FIG. 5, and FIG. 7 shows some explanatory waveforms.

Referring now to the drawings, FIG. 1 shows electrotherapeutic apparatus constructed in accordance with the present invention and comprising a generator 1 taking power from a mains supply 2 and supplying energising current to a pair of electrodes 3 and 4. In FIG. 1 electrode 3 is an active electrode and is shown in greater detail in FIGS. 2 and 3, whilst electrode 4 is a neutral electrode.

Referring now to FIGS. 2 and 3, electrode 3 comprises a substantially rectangular sheet of flexible elastomeric material carrying on the operative face thereof, that is the face which is to be applied to a ptient's skin, three individual electrodes 6. Each electrode 6 comprises a metallic strip bonded or adhered to a thin electrically insulating sheet 7 of thermoplastics material which is in turn bonded or adhered to the elastomeric sheet 5. Each strip electrode 6 is connected to an appropriate connector 8 located at one end of the sheet 5. It will be seen that each electrode 6 has a plurality of circular apertures 9 therein which expose the insulating sheet 7. In FIG. 3 of the drawings it will also be seen that sheet 5 has a plurality of circular portions 10 removed therefrom so as to provide a series of openings in the sheet 5 which are in register with the circular apertures 9 in the strip electrodes 6. The flexible sheet 7 thus forms a window at each of the openings in sheet 5. A disc-like ferrite magnetic core 11 is housed in each opening 10 in the sheet 5 and is secured by a suitable adhesive to the sheet 7. One opening 10 is shown without a magnetic core purely for the purposes of illustration. Each magnetic core 11 has a substantially annular recess surrounding a central pole-piece about which is wound a wire coil in turn connectable to connectors 13 located adjacent the connectors 8. The coils of the cores associated with a strip electrode 6 are connected in series. The neutral electrode 4 may be made from a backing sheet similar to sheet 5 of electrode 3 and which carries only a single metallic strip electrode. However it is also possible for the electrode 4 to carry ferrite cores similar to those mounted in the electrode 3. It will be appreciated that in operation of the device the electrodes 3 and 4 will in one mode of operation set up high frequency fields therebetween, the generation of such fields requiring the use of two electrodes whilst in the other mode of operation of the apparatus the magnetic cores set up oscillating magnetic fields in the patient's body with each core operating independently.

In use the electrodes 3 and 4 are placed on either side of, or at least at spaced positions on, the portion of a patient's body to be treated. This is shown diagrammatically in FIG. 4. The generator 1 is desired to supply power to the electrodes 3 and 4 in such a manner that the patient can be treated simultaneously in the two entirely different ways already mentioned. Thus, by means of the strip electrode 6 and the neutral electrode 4 that portion of the patient's body located between the two electrodes 3 and 4 can be subjected to a UHF electric field whilst by means of the magnetic cores 11 that portion of the patient's body adjacent the cores 11 can be treated with either low or high frequency magnetic fields. Thus the generator 1 comprises circuits for supplying appropriate energising currents to both the magnetic cores 11 and the strip electrodes 6 and for controlling the relationship between the application of the two types of treatment.

Referring now to FIG. 5 of the accompanying drawings it can be seen that the main supply 2 (shown in FIG. 1) is connected via a suitable switch 20 to the input winding of a transformer 21, the output winding of which is connected to two terminals of a diode bridge 22, the outputs of which supply a full-wave rectified output to a power adjust circuit 23. A suitable filter or smoothing circuit may be inserted between the diode bridge and circuit 23. The output from circuit 23 is supplied to a drive circuit 25 which in turn gives an output in the form of a pulsed waveform which is supplied to the coils of the magnetic cores 11 of the active electrode 3. The frequency of the output waveform from the driver circuit 25 is controlled in a manner which will be described hereinafter so as to coordinate application of magnetic energy to the patient with the application of UHF fields. Thus, the circuit for driving the strip electrodes 6 so as to provide a varying HF electrical field between the strip electrodes 6 and the neutral electrode 4 comprises a quartz crystal oscillator 30 adapted to generate a 27.125 MHz. output signal which is supplied to an impedance adaptor 31 and then to the neutral electrode 4 via one line and via another line to three similar matching circuits indicated at 34. Each matching circuit is connected to one of the strip electrodes forming part of the active electrode 3.

The strip electrodes 6 are energised intermittently at intervals determined by an impulse generator 40 in turn controlled by a circuit comprising a variable oscillator 41 providing a train of pulses to a frequency division circuit 42. The output of the frequency division circuit 42 is associated with an impulse select circuit 43 and is connected to a divide-by-three circuit 44 one output of which is taken to the driver circuit 25 for gating the output signals to the coils of the magnetic cores 11 in the active electrode 3. The three outputs of the divide-by-three circuit 44 are also supplied to the impulse generator 40 to control the latter.

It will thus be seen that in operation of the device a patient will be subjected to alternate bursts of magnetic energy from cores 11 and their associated coils and high frequency electric fields generated between strip electrodes 6 and netural electrode 4.

Referring now to FIG. 6 this shows the circuit components of the block diagram of FIG. 5. Thus, in this figure integers which are common to those of FIG. 5 have been given the same reference numerals. The output of diode bridge 22 is connected to the power adjust circuit 23 via a display circuit generally indicated at 50 and including five parallel photodiodes 51; the outputs of the three central ones of the photodiodes 51 are connected to contacts of a three-position switch 52 which is ganged to a switch 53 in the power adjust circuit 23. The power adjust circuit 23 includes a voltage regulator 24 one output of which is selectably connectable by switch 53 to different points in a resistor chain of four resistors 54 connected in series so that the output power of the circuit can be set at three different levels by switch 53. When the apparatus is in use adjustment of the main switch 53 will correspondingly adjust the switch 52 so that a visible indication will be given of the power selected by the power adjust circuit 23 by the photodiode connected into circuit by switch 52 lighting up. Naturally there are many alternative methods of giving a visible indication.

The output of the power adjust circuit 23 is taken to the driver circuit 25 which comprises three transistors 55, 56, 57. The transistor 55 is a control transistor the base of which is connected to the Q-output of a flip-flop 58 whilst the transistors 56 and 57 are connected in cascade. One input of flip-flop 58 is connected directly to one output of the divide-by-three circuit 44 whilst the other input is connected to a pair of logic gates 59 and 60 connected in series. Logic gate 59 has its two inputs connected to the same output of divide-by-three circuit 44 as the other input of flip-flop 58. The variable oscillator 41 supplies a train of pulses of selected frequency to the input of frequency division circuit 42. As shown this circuit is capable of giving a range of output frequencies. In the present embodiment these are 640, 320, 160, 80, 64, 32, 16 and 8. The divide-by-three circuit 44 takes the train of pulses from the frequency division circuit 42 and it distributes these sequentially to three output points 65, 66 and 67 under the control of the I.C. circuit type 4518 shown at 46 which basically provides the impulse select circuit 43. This can be seen from FIG. 7 where waveform A shows the output of circuit 42, and B the outputs from the output points 65, 66 and 67. The three signals from the outputs 65, 66 and 67 are respectively applied to the bases of transistors 68, 69 and 70 in impulse generator 40 which in turn feed the matching circuit 34 for application to the strip electrodes 6. The signals from the divide-by-three circuit and the impulse generator 40 are intended to control the application to the strip electrodes 6 of the high frequency signals generated by the oscillator 30. As can be seen from FIGS. 5 and 6 an output of oscillator 30 is taken to the neutral electrode 4, and as can be seen from FIG. 6 an output is also connected to the bases of three power transistors 71, 72 and 73 for application to the electrode 6 under the control of the signals from the impulse generator 40.

The relationship between the two forms of energy which can be applied to the patient can best be understood by reference to FIG. 7c. This shows two separate ways in which the phase and frequency of the high-frequency electrical signals which are supplied to strip electrodes 6 can be related to the phase and frequency of the current for driving the coils of the cores 11 to generate the magnetic field. In the two waveforms shown the current to coils of the cores 11 is represented by hatching. Thus, in the first of the two waveforms there is applied to the patient magnetic energy and UHF fields in bursts which are of the same frequency but with no overlap between the two modes of treatment although the patient is continuously treated with one or the other forms of energy. In the second waveform it will be seen that the frequency of application of the magnetic field via the cores 11 is half of that of the application of the electrical field by the strip electrodes 6 and neutral electrode 4. It will of course be fully appreciated that by suitably selecting the logic circuitry interconnecting the output of the divide-by-three circuit 44 and the driver circuit 25 that the relationship between the application of the magnetic energy and of the UHF fields can be varied as desired. However in the present embodiment it will be realised that there is always some fixed relationship as the two forms of energy are controlled by control signals derived from a single oscillator. Furthermore it is possible to alter the intensity of the magnetic field independently of the other mode of treatment.

The present invention, applicable to all forms of electrotherapeutic apparatus, is particularly intended for use with low voltage apparatus utilising voltages of less than 50 volts and energies of less than 100 mw per cm$^2$ of receiving surface, thereby enabling harmful thermal effects to be avoided, bulk to be considerably reduced with regard to high voltage apparatus and antenna or applicator electrodes to be used which can be placed in contact with the patient's body.

When the apparatus described herein is in use a patient will not feel the magnetic or electrical fields generated by the apparatus. However the cores 11 and their associated coils will in operation produce a degree of vibration which can be felt by the patient and will provide confirmation to him that he is in fact being treated.

Figure 8:
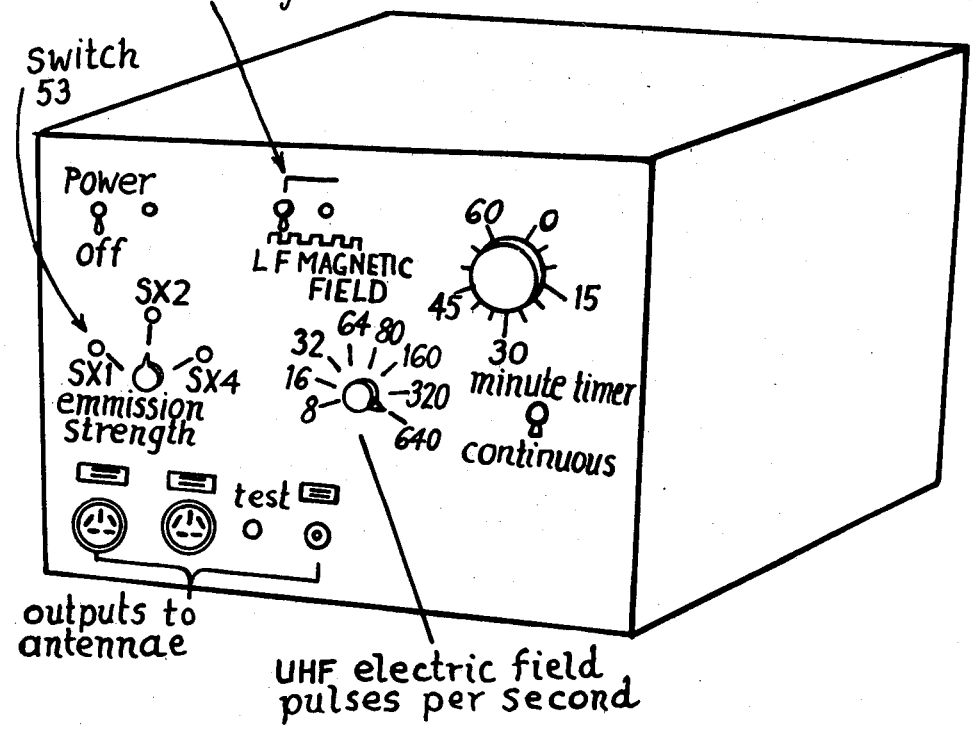

FIG. 8 is a perspective view of the apparatus just described and shows a substantially rectangular casing.

Referring now to FIG. 8 of the accompanying drawings, this shows the outward appearance of a practical embodiment of the electrotherapeutic apparatus which has been described with reference to FIGS. 1 to 7.

I claim:

1. Electrotherapeutic apparatus comprising means for generating and applying to a patient's body a pulsed high frequency electrical field, means for generating and applying to the patient a pulsed magnetic field independent from the electrical field, and means for coordinating the pulses of the magnetic field with the pulses of the electrical field, whereby the pulses of the magnetic and electrical fields can be applied in a predetermined relationship to provide enhanced antispasmodic and analgesic effects and maximize healing effect.

2. Apparatus as claimed in claim 1, wherein the means for applying the high frequency electrical field and the magnetic field comprises an applicator electrode applicable directly to a patient's body and which includes at least one magnetic coil for producing the pulsed magnetic field and at least one active electrode for applying the pulsed high-frequency electrical field.

3. Apparatus as claimed in claim 2, and including a neutral electrode arranged to cooperate with said at least one active electrode in the production of said high-frequency electrical field.

4. Apparatus as claimed in claim 2 or 3, wherein the means for generating the pulsed electrical field comprises a circuit for producing high-frequency electrical signals which are fed to said at least one active electrode, wherein the means for generating and applying the pulsed magnetic field includes a drive circuit for supplying electrical output signals to said at least one magnetic coil of said applicator electrode, and wherein the means for coordinating the pulses of the electrical and magnetic fields comprises control means connected to said high-frequency signal producing circuit and to said drive circuit for providing said predetermined relationship.

5. Apparatus as claimed in claim 4, and including a plurality of magnetic coils and a plurality of active electrodes in said applicator electrode.

6. Apparatus as claimed in claim 5, wherein said applicator electrode comprises a flexible sheet.

7. Apparatus as claimed in claim 6 wherein each said magnetic coil comprises a magnetic core mounted in an opening in said sheet.

8. Apparatus as claimed in claim 7, wherein each magnetic core has a substantially annular recess surrounding a central pole-piece about which is wound a wire coil.

9. Apparatus as claimed in claim 7, wherein the neutral electrode comprises at least one strip electrode incorporated in a flexible sheet.

10. Apparatus as claimed in claim 9, wherein the control means includes an impulse generator controlled by the output of a frequency divider circuit one input of which is connected to the output of an oscillator, said impulse generator in operation controlling the application of the high frequency electrical singals to said active electrodes.

11. Apparatus as claimed in claim 10, including an impulse select circuit for controlling the operation of the frequency divider circuit.

12. Apparatus as claimed in claim 11, wherein the means for generating the high frequency electrical signals includes an oscillator connected to said at least one active electrode by a matching circuit, the operation of said at least one matching circuit being controlled by said impulse generator.

13. Apparatus as claimed in claim 5, wherein said active electrodes comprise conductive strips mounted on said flexible sheet.

14. Apparatus as claimed in claim 1, wherein said predetermined relationship involves at least one of (a) the pulses of the magnetic field being disposed between pulses of the electrical field and (b) the pulses of the magnetic field being in overlapping relationship with pulses of the electrical field.

15. Electrotherapeutic apparatus comprising:
(a) a first circuit means for generating high-frequency electrical signals,
(b) applicator means for applying said signals to a patient's body to produce therein a pulsed high-frequency predominently electrical field,
(c) a second circuit means for generating and for applying to a patient's body a pulsed magnetic field which is independent from said electrical field,
(d) said second circuit means including
(i) a first circuit for generating electrical output signals,
(ii) a drive circuit for gating said electrical output signals from said first circuit to produce an output wave form and
(iii) another circuit which is energized by said output wave form to produce said pulsed magnetic field, and (e) a third circuit means connected to said first circuit means and to said drive circuit to coordinate the output wave form from said drive circuit with an output wave form of said high-frequency electrical signals from said first circuit means, whereby the pulses of said magnetic field can be applied in a predetermined relationship with the pulses of said electrical field to provide enhanced antispasmodic and analgesic effects and maximize healing effect.

16. Apparatus as claimed in claim 15, wherein said predetermined relationship involves at least one of (a) the pulses of the magnetic field being disposed between pulses of the electrical field and (b) the pulses of the magnetic field being in overlapping relationship with pulses of the electrical field.

17. Apparatus as claimed in claim 15, wherein said third circuit means for coordinating the output wave forms from the drive circuit and said first circuit means comprises an impulse generator controlled by the output of a frequency divider circuit one input of which is connected to the output of a variable oscillator.

18. Apparatus as claimed in claim 17, wherein said third circuit means further comprises an impulse select circuit for controlling the operation of the frequency divider circuit.

19. Apparatus as claimed in claim 18, wherein said first circuit means includes an H.F. oscillator and at least one matching circuit which is connected to said oscillator and whose operation is controlled by said impulse generator.

20. Apparatus as claimed in claim 15, wherein said applicator means comprises at least one active electrode which is applicable directly to a patient's body and which includes said another circuit of said second circuit means, said another circuit comprising at least one magnetic coil, and a neutral electrode which co-operates with the active electrode in the production of the high-frequency electrical field is applicable directly to a patient's body.

21. Apparatus as claimed in claim 20, wherein said active electrode comprises a flexible sheet, at least one conductive strip mounted on said sheet with said at least one magnetic coil being mounted in a recess in said sheet and comprising a magnetic core about which is wound a wire coil.

* * * * *